United States Patent [19]

Mahler et al.

[11] Patent Number: 4,794,914

[45] Date of Patent: Jan. 3, 1989

[54] SHOCK WAVE GENERATOR FOR AN APPARATUS FOR NON-CONTACTING DISINTEGRATION OF CALCULI IN THE BODY OF A LIFE FORM

[75] Inventors: Matthias Mahler, Erlangen; Sylvester Oppelt, Bamberg; Manfred Rattner, Buckenhof, all of Fed. Rep. of Germany

[73] Assignee: Siemens Aktiengesellschaft, Berlin and Munich, Fed. Rep. of Germany

[21] Appl. No.: 55,318

[22] Filed: May 29, 1987

[30] Foreign Application Priority Data

Jun. 5, 1986 [DE] Fed. Rep. of Germany ....... 3618903

[51] Int. Cl.[4] .............................................. A61B 17/22

[52] U.S. Cl. .................................. 128/24 A; 367/175

[58] Field of Search ..................... 128/24 A, 328, 804; 367/140–142, 156, 163, 174, 175; 181/150, 151, 142, 172; 381/159, 193

[56] References Cited

U.S. PATENT DOCUMENTS

| | | | |
|---|---|---|---|
| 2,561,368 | 7/1951 | Hayes et al. | 367/175 |
| 2,978,669 | 4/1961 | Harris | 367/175 |
| 3,495,211 | 2/1970 | Harris | 367/174 |
| 4,655,220 | 4/1987 | Hahn et al. | 128/328 |
| 4,697,588 | 10/1987 | Reichenberger | 128/328 |

*Primary Examiner*—Ruth S. Smith

[57] ABSTRACT

The invention is directed to a shock wave generator for an apparatus for non-contacting disintegration of calculi in the body of a life form which includes a housing filled with a liquid, a membrane closing the housing and connected thereto along the edge thereof, and a device for pulse-like driving of the membrane. In order to suppress overstressing of the membrane and deformations of the membrane which are diletorious in view of the focussability of the shock waves, a tubular spring resilient in the moving direction of said membrane are provided between said housing and said membrane, said membrane being connected to said housing with said resilient spring in a fashion essentially free of bending moment.

2 Claims, 3 Drawing Sheets

SHOCK WAVE GENERATOR FOR AN APPARATUS FOR NON-CONTACTING DISINTEGRATION OF CALCULI IN THE BODY OF A LIFE FORM

BACKGROUND OF THE INVENTION

1. Field of the Invention

The invention is directed to a shock wave generator for an apparatus for non-contacting disintegration of calculi in the body of a life form, comprising a housing filled with a liquid, a membrane closing said housing and connected thereto along the edge thereof, and comprising means for pulsed driving of the membrane.

2. Description of the Prior Art

German published patent application No. 33 12 014 discloses such a shock wave generator. In the known shock wave generator, the membrane is electromagnetically driven. The shock waves emitted by this membrane are focussed onto the calculus, for example, the renal calculus of a human, by means of suitable measures in order to disintegrate this calculus.

The membrane of the known shock wave generator is secured such to the housing that it is firmly clamped along its entire edge. This leads thereto that the membrane, when driven pulse-like, is exposed to sudden bending stresses which can lead to overstressing of the membrane and, finally, to the outage thereof. Also disadvantageously occurring as a consequence of the deformations of the membrane connected to the bending stresses is that the shock waves generated with the known shock wave generator deviate from the desired ideal with respect to the shape and the pressure distribution in the pressure front, this leading to the fact that the shock waves can be focussed onto the calculus to be disintegrated to only a limited degree, i.e. the obtainable focus exhibits a relatively large three-dimensional extent, this being deleterious to the efficiency of the shock waves.

SUMMARY OF THE INVENTION

An object of the invention is to provide a shock wave generator of the type described above such that overstressing of the membrane and deformations of the membrane which are injurious with respect to the focusability of the shock waves are suppressed.

This object is achieved in accord with the invention in that means which are resilient in the direction of motion of the membrane are provided between the housing and the membrane, the membrane being connected to the housing with these means essentially free of bending moment. As a result of this measure, the overall membrane can move in the direction of the force driving it under the influence of the means for the drive thereof. Deformations of the membrane which derive from the fashion in which it is fastened to the housing are thus avoided to the greatest possible degree given the shock wave generator of the invention. The membrane therefore has an enhanced useful life in comparison to the known shock wave generator and the shock wave generated with the shock wave generator of the invention can be focussed better.

In accord with an embodiment of the invention, the elastic means are formed by a rubber spring. The rubber spring can thereby be expediently connected to the membrane and the housing integrally, for example, by vulcanization, whereby both the fastening of the membrane to the housing as well as a good sealing effect between the two is achieved in a simple way. An especially favorable stressing of the rubber spring derives when, in accord with a modification of the invention, this is arranged between surfaces of the housing and of the membrane which lie opposite one another in the moving direction of the membrane, whereby an arrangement wherein the rubber spring and the vulcanizations existing between this rubber spring and the housing or the membrane are essentially stressed for pressure is to be preferred.

Further embodiments of the invention provide that the resilient means are respectively fashioned as a saucer spring or as a tubular spring attached to the edge of the membrane, whereby these resilient means can comprise a zig-zag, meander or wavy cross-section in order to assure an adequate resiliency in the moving direction of the membrane.

In view of a simple manufacture and assembly of the shock wave generator of the invention, finally, it is advantageous when the resilient means are fashioned of one piece with the membrane.

BRIEF DESCRIPTION OF THE DRAWINGS

Exemplary embodiments of the invention are shown in the attached drawings. Shown are.

DESCRIPTION OF THE PREFERRED EMBODIMENTS

Figure 1:
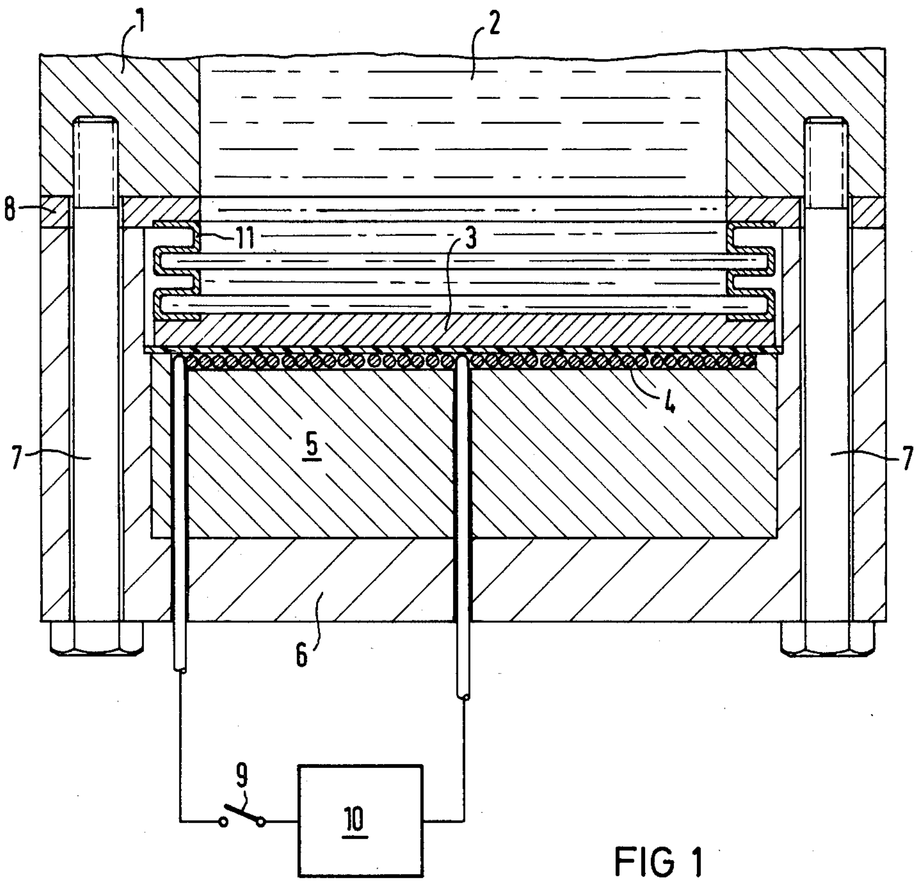
FIG. 1 is a longitudinal section through a shock wave generator of the invention.

The shock wave generator of the invention shown in FIG. 1 comprises a housing 1 which surrounds a space 2 filled with a liquid, this space 2 being closed by a plate-shaped membrane 3. A helically wound coil 4 lying opposite the latter is arranged on an insulator 5 which is accepted in a cap 6 which is secured to the housing 1 by means of screws 7. At the same time, the membrane 3 is connected to the housing 1 along its edge via a ring 8 which is held by means of the screws between the housing 1 and the cap 6.

The membrane 3 is composed of an electrically conductive material and can be driven pulse-like by means of the coil 4 in that the latter is connected to a schematically shown high-voltage supply 10 via suitable switch means 9. The high-voltage supply 10 emits a pulse-like current surge to the coil 4, whereby the latter builds up a magnetic field. At the same time, a current of opposite direction is induced in membrane 3, this current producing an opposing magnetic field. The membrane 3 is thus suddenly repelled from the coil 4, whereby a shock wave arises in the liquid situated in the space 2, this shock wave being focussed on a calculus with means that are not shown and disintegrating this calculus.

In the shock wave generator of the invention, means which is resilient in the moving direction of the membrane 3 is provided between the housing 1 and the membrane 3, this elastic means being fashioned as a tubular rubber spring 11 attached to the edge of the membrane 3 and connecting the membrane 3 to the housing 1 via the ring 8 in a fashion essentially free of bending moment. In order to guarantee an adequate resiliency in the moving direction of the membrane 3, the hollow spring 11 comprises a meander-like cross-section. The tubular spring 11 is secured both to the edge of the membrane as well as to the ring 8 by liquid-tight welds.

The exemplary embodiments in FIGS. 2–5 deviate from the exemplary embodiment of FIG. 1 only with respect to the fashioning of the resilient means, for which reason identical parts are provided with the respectively same reference numerals as in FIG. 1.

Figure 2:
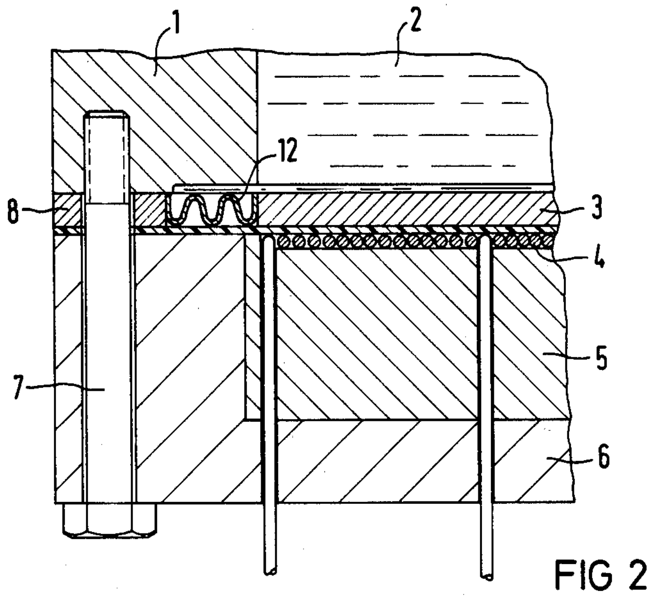
FIGS. 2–5 are partial longitudinal sections through further shock wave generators of the invention.

Given the shock wave generator of the invention shown in FIG. 2, the resilient means is fashioned as a saucer spring 12 having a wavy cross-section serving the purpose of assuring an adequate resiliency in moving direction of the membrane 3. The saucer spring 12 has its inside edge secured to the edge of the membrane 3 and has its outer edge secured to the ring 8 in liquid-tight fashion by soldering.

Figure 3:
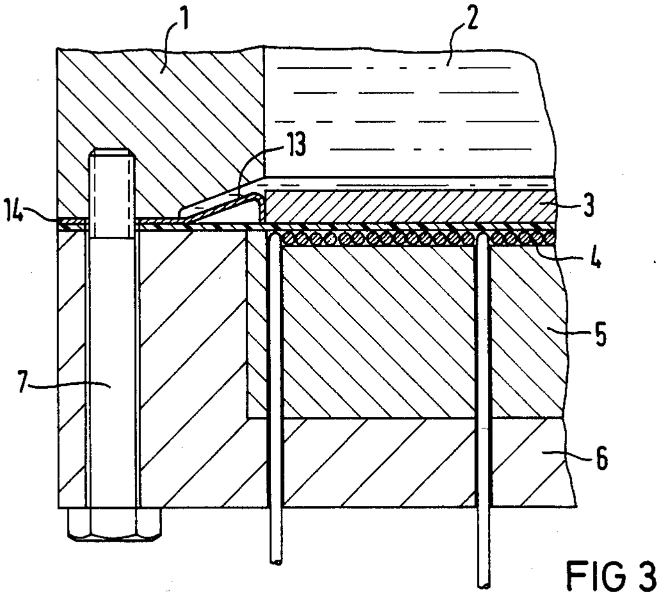

In the shock wave generator of the invention of FIG. 3, the resilient means is fashioned as conical saucer springs 13. This embodiment is especially advantageous when small amplitudes of the membrane 3 are the only amplitudes occurring. The saucer spring 13 has its inside edge secured to the membrane 3 by means of a liquid-tight soldering, whereas its outer edge is secured with a planar flange 14 which is held between the cap 6 and the housing 1 by the screws 7.

Figure 4:
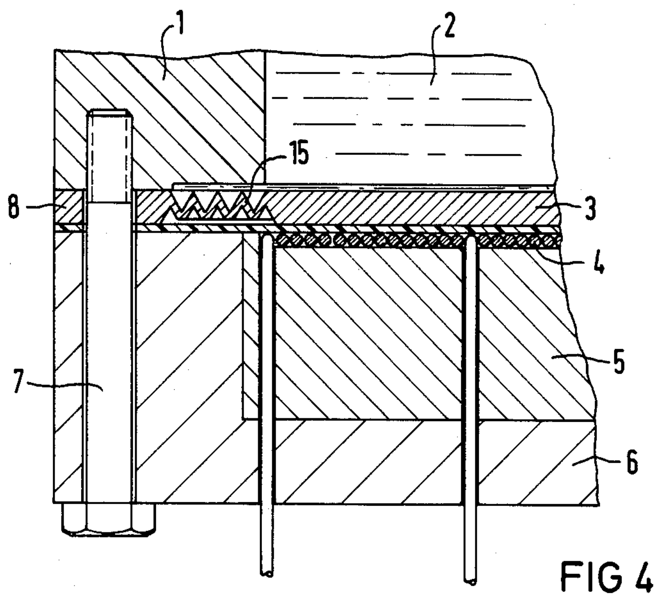

The shock wave generator of the invention in accord with FIG. 4 comprises a membrane 3 at whose edge the resilient means fashioned as a saucer-spring-like annular segment 15 with zig-zag cross-section is fashioned of one piece therewith. The ring 8 via which the membrane 3 is held at the housing 1 by the screws 7 is applied of one piece to the outer edge of the annular segment 15.

Figure 5:
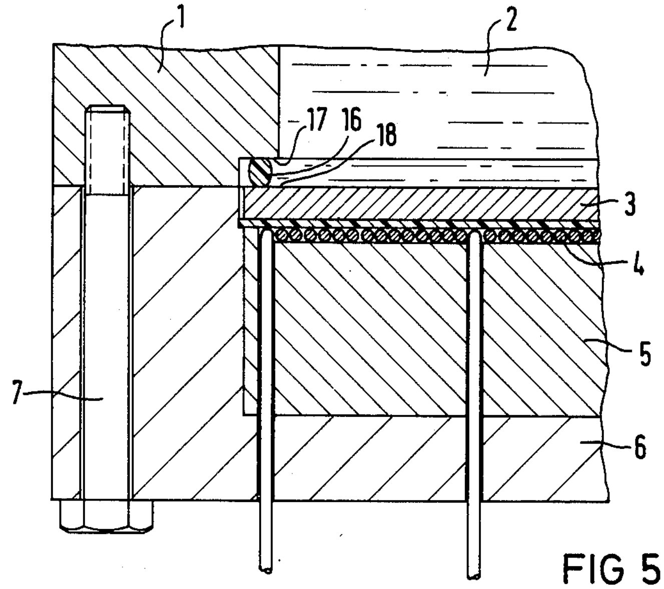

FIG. 5, finally, shows a shock wave generator of the invention wherein the resilient means are formed by a ringshaped-rubber spring 16 having a roughly oval cross-section which is arranged between faces 17 and 18 of the housing 1 and of the membrane 3 facing one another in moving direction of the membrane 3 and which is connected to the surfaces 17 and 18 by vulcanizing. The arrangement is thereby undertaken such that the rubber spring 16 is compressed given pulse-like drive of the membrane 3, whereby inadmissible stresses of the connections of the rubber spring 16 cylinder to the membrane 3 or, respectively, to the housing 1 produced by vulcanizing are avoided.

The resilient means can also be fashioned in some way differing from the ways set forth in the exemplary embodiments insofar as it is merely assured that these means have an adequate resiliency in moving direction of the membrane in order to allow this membrane to move as a totality without being exposed to bending moments.

The connection of the resilient means to the membrane or, respectively, to the housing can also be executed non-positively or, respectively, with friction locks differing from the exemplary embodiments.

As is apparent from the foregoing specification, the invention is susceptible of being embodied with various alterations and modifications which may differ particularly from those that have been described in the preceding specification and description. It should be understood that we wish to embody within the scope of the patent warranted hereon all such modifications as reasonably and properly come within the scope of our contribution to the art.

We claim as our invention:

1. A shock wave generator for an apparatus for non-contacting disintegration of calculi in the body of a life form, including a housing containing a volume filled with a liquid as a transmission medium for shock waves, a membrane terminating the volume at one side and having a circumferential edge, and means for pulsingly driving the membrane in a moving direction towards the volume, the improvement comprising, a spring means being resilient in the moving direction of said membrane and attached to said circumferential edge of said membrane for connecting said membrane to said housing in a fashion allowing said membrane to be driven in the direction of movement essentially free of bending stresses exerted on said membrane by said spring means, said spring means comprising a tubular spring including a meander-like cross-section and being arranged between surfaces of said housing and said membrane which lie opposite one another in the moving direction of said membrane.

2. A shock wave generator for an apparatus for non-contacting disintegration of calculi in the body of a life form, including a housing containing a volume filled with a liquid as a transmission medium for shock waves, a membrane terminating the volume at one side and having a circumferential edge, and means for pulsingly driving the membrane in a moving direction towards the volume, the improvement comprising, a spring means being elastic in the moving direction of said membrane and attached to said circumferential edge of said membrane for connecting said membrane to said housing in a fashion allowing said membrane to be driven in the direction of movement essentially free of bending stresses exerted on said membrane by said spring means, said spring means comprising a rubber spring being arranged between surfaces of said housing and said membrane which lie opposite one another in the moving direction of said membrane.

* * * * *